United States Patent
Kolpashchikov

(10) Patent No.: US 8,853,134 B2
(45) Date of Patent: *Oct. 7, 2014

(54) MICROARRAYS OF BINARY NUCLEIC ACID PROBES FOR DETECTING NUCLEIC ACID ANALYTES

(75) Inventor: Dmitry Kolpashchikov, Winter Park, FL (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/146,626

(22) PCT Filed: Jan. 28, 2010

(86) PCT No.: PCT/US2010/022428
§ 371 (c)(1),
(2), (4) Date: Aug. 26, 2011

(87) PCT Pub. No.: WO2010/088404
PCT Pub. Date: Aug. 5, 2010

(65) Prior Publication Data
US 2012/0040867 A1    Feb. 16, 2012

Related U.S. Application Data

(60) Provisional application No. 61/147,993, filed on Jan. 28, 2009.

(51) Int. Cl.
| | |
|---|---|
| *C40B 40/06* | (2006.01) |
| *C40B 80/00* | (2006.01) |
| *C12Q 1/68* | (2006.01) |
| *B01J 19/00* | (2006.01) |
| *C40B 50/18* | (2006.01) |

(52) U.S. Cl.
CPC ........ *C40B 80/00* (2013.01); *B01J 2219/00659* (2013.01); *B01J 2219/0061* (2013.01); *B01J 2219/00722* (2013.01); *C12Q 1/6837* (2013.01); *B01J 19/0046* (2013.01); *C40B 50/18* (2013.01); *B01J 2219/00612* (2013.01); *B01J 2219/00608* (2013.01); *B01J 2219/00529* (2013.01)
USPC .............................................. 506/13; 506/16

(58) Field of Classification Search
USPC .......................................................... 506/13
See application file for complete search history.

(56) References Cited

U.S. PATENT DOCUMENTS

| 6,413,722 B1 | 7/2002 | Arnold et al. |
| 2002/0172960 A1 | 11/2002 | Bao et al. |

(Continued)

FOREIGN PATENT DOCUMENTS

| EP | 0853129 | * 7/1998 | ............... C12Q 1/68 |
| WO | 92/20823 A1 | 11/1992 | |

(Continued)

OTHER PUBLICATIONS

Kolpashchikov, Binary Probes for Selective Nucleic Acid Recognition, 2007, Book of Abstracts:2007.*

(Continued)

*Primary Examiner* — Larry Diggs
*Assistant Examiner* — Karla Dines
(74) *Attorney, Agent, or Firm* — Timothy H. Van Dyke; Beusse, Wolter, Sanks & Maire, P.A.

(57) ABSTRACT

Some embodiments of the invention are directed to a microarray of binary nucleic acid probes for the detection of one or a plurality of nucleic acid analytes in a complex sample in a single high throughput assay with extraordinary specificity under physiologic conditions. Any binary nucleic acid probes that generate a detectable signal when bound to analyte are suitable for use in the microarrays, including binary deoxyribozyme or ribozyme probes; nonenzymatic binary probes for fluorescent detection, nonenzymatic binary dye-binding probes, and binary split enzyme peroxidase probes for visual detection of nucleic acids. The invention is also directed to new non nonenzymatic binary probes that bind to reporter oligonucleotides.

7 Claims, 11 Drawing Sheets

NONENZYMATIC BINARY NUCLEIC ACID PROBES BINDING TO MOLECULAR BEACONS

(56) References Cited

U.S. PATENT DOCUMENTS

2007/0231810 A1 10/2007 Todd et al.
2009/0176318 A1 7/2009 Kolpashchikov

FOREIGN PATENT DOCUMENTS

WO 2007/115242 A2 10/2007
WO 2008/054834 A2 5/2008
WO 2010/059944 A1 5/2010

OTHER PUBLICATIONS

Xiao et al., Catalytic Beacons for the Detection of DNA and Telomerase Activity, J.Am. Chem. Soc., 2004, 126, pp. 7430-7431.*

Kolpashchikov, A Binary Deoxybibozyme for Nucleic Acid Analysis, Chembiochem, Nov. 23, 2007, 8(17), pp. 2039-2042.*

Babendure et al., "Aptanners Switch on Fluorescence of Triphenylmethane Dyes", "J. Am. Chem. Soc.", Nov. 8, 2003, pp. 14716-14717, vol. 125, Publisher: American Chemical Society, Published in: US.

Bonnet et al, "Thermodynamic basis of the enhanced specificity of structured DNA probes", "Proc. Natl. Acad. Sci.", May 1999, pp. 6171-6174, vol. 96, Published in: US.

Kolpashchikov, Dmitry M., "Binary Malachite Green Aptamer for Fluorescent Detection of Nucleic Acids", Aug. 19, 2005, pp. 12442-12443, vol. 127, Publisher: American Chemical Society, Published in: US.

Kolpashchikov, Dmitry M., "A Binary DNA Probe for Highly Specific Nucleic Acid Recognition", "J. Am. Chem. Soc.", Jul. 21, 2006, pp. 10625-10628, vol. 128, Publisher: American Chemical Society, Published in: US.

Kolpashchikov, Dmitry M., "A Binary Deoxyribozyme for Nucleic Acid Analysis", "ChernBioChern", 2007, pp. 2039-2042, vol. 8, Publisher: Wiley-VCH Verlag GmbH & Co., Published in: Germany.

Kolpashchikov, Dmitry M., "Split DNA Enzyme for Visual Single Nueleotide Polymorphism Typing", "Journal of American Chemical Society", Mar. 12, 2008, pp. 2934-2935, vol. 130, No. 10.

Marras et al, "Real-time assays with molecular beacons and other fluorescent nucleic acid hybridization probes", "Clinica Chimica Acta", Aug. 18, 2005, p. 48-60, vol. 363, Publisher: Elsevier B.V.

Mokany et al., "MNAzymes, a Versatile New Class of Nucleic Acid Enzymes That Can Function as Biosensors and Molecular Switches", "J. Am. Chem. Soc.", 2010, pp. 1051-1059, vol. 132, No. 3, Publisher: American Chemical Society.

Isa, "International Preliminary Report on Patentability for Corresponding International Application No. PCT/US2010/022428", Aug. 2, 2011, pp. 1-8, Published in: Switzerland.

Isa, "International Search Report and Written Opinion for Corresponding International Application No. PCT/US10/22428", Mar. 19, 2010, pp. 1-12, Published in: US.

Sando et al., "Light-Up HoechstDNA AptamerPair: Generation of an Aptamer-Selective Fluorophore from a Conventional DNA-Staining Dye", "ChemBioChem", 2007, pp. 1795-1803, vol. 8, Publisher: Wiley-VCH Verlag GmbH & Co., Published in: Germany.

Tyagi et al., "Molecular Beacons: Probes that Fluoresce upon Hybridization", "Nature Biotechnology", Mar. 1996, pp. 303-308, vol. 14, Publisher: Nature Publishing Group.

Kolpashchikov, D. et al., "Boolean Control of Aptamer Binding States", J. Am. Chem. Soc., 2005, vol. 127, pp. 11348-11351.

* cited by examiner

MICROARRAY WITH BINARY ENZYMATIC PROBE COMPLEX

FIG. 4 MICROARRAY WITH ONE STRAND OF MB-BINDING BINARY PROBE

FIG. 5 BINARY DEOXYRIBOZYME PROBE STRAND STRUCTURE

FIG. 7 BINARY OLIGONUCLEOTIDE PEROXIDASE-LIKE PROBE

NONENZYMATIC BINARY NUCLEIC ACID PROBES BINDING TO MOLECULAR BEACONS

FIG. 9 BINARY DYE-BINDING PROBE

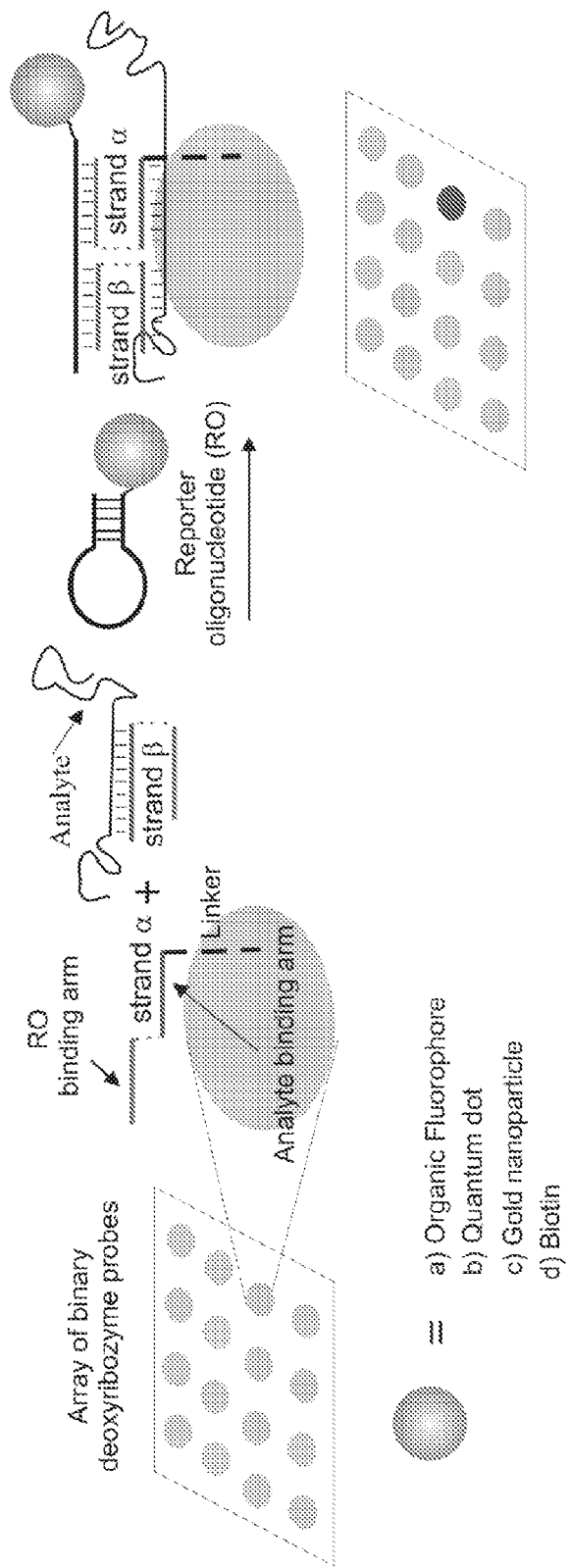
FIG. 11  BINARY REPORTER OLIGONUCLEOTIDE-BINDING PROBE

SEQUENCE LISTING

```
<160> NUMBER OF SEQ ID NOS: 19

<210> SEQ ID NO 1
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 1
ctcttcagcg atcagttctt ctctctccat gagag                              35

<210> SEQ ID NO 2
<211> LENGTH: 38
<212> TYPE: DNA
<213> ORGANISM: Artificial Sequence
<220> FEATURE:
<223> OTHER INFORMATION: Synthetic construct

<400> SEQUENCE: 2
tgggtctcgc acccattgaa ctgcacccat gttagtga                           38

<210> SEQ ID NO 3
<211> LENGTH: 15
<212> TYPE: DNA
<213> ORGANISM: Artificial Sequence
<220> FEATURE:
<223> OTHER INFORMATION: Synthetic construct

<400> SEQUENCE: 3
gagaaggata tcact                                                    15
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
atggagagag tgggtgcgag                                               20

<210> SEQ ID NO 5
<211> LENGTH: 17
<212> TYPE: DNA
<213> ORGANISM: Artificial Sequence
<220> FEATURE:
<223> OTHER INFORMATION: Synthetic sequence

<400> SEQUENCE: 5
gggtagggcg ggttggg                                                  17

<210> SEQ ID NO 6
<211> LENGTH: 8
<212> TYPE: DNA
<213> ORGANISM: Artificial Sequence
<220> FEATURE:
<223> OTHER INFORMATION: Synthetic sequence

<400> SEQUENCE: 6 gggtaggg                                                             8

<210> SEQ ID NO 7
<211> LENGTH: 10
<212> TYPE: DNA
<213> ORGANISM: Artificial Sequence
<220> FEATURE:
<223> OTHER INFORMATION: Synthetic sequence

<400> SEQUENCE: 7
ccgtgtcctg                                                          10

<210> SEQ ID NO 8
<211> LENGTH: 8
<212> TYPE: DNA
<213> ORGANISM: Artificial Sequence
<220> FEATURE:
<223> OTHER INFORMATION: Synthetic sequence

<400> SEQUENCE: 8 gggttggg                                                             8

<210> SEQ ID NO 9
<211> LENGTH: 8
<212> TYPE: DNA
<213> ORGANISM: Artificial Sequence
<220> FEATURE:
<223> OTHER INFORMATION: Synthetic sequence

<400> SEQUENCE: 9 gtgcaccc                                                             8

<210> SEQ ID NO 10
<211> LENGTH: 10
<212> TYPE: DNA
<213> ORGANISM: Artificial Sequence
<220> FEATURE:
<223> OTHER INFORMATION: Synthetic sequence
```

<400> SEQUENCE: 10
ccgtgtcctg                                                              10

<210> SEQ ID NO 11
<211> LENGTH: 34
<212> TYPE: DNA
<213> ORGANISM: Artificial Sequence
<220> FEATURE:
<223> OTHER INFORMATION: Synthetic sequence

<400> SEQUENCE: 11
tggcttcgcc cagggtgcac caggacacgg tttt                                   34

<210> SEQ ID NO 12
<211> LENGTH: 15
<212> TYPE: DNA
<213> ORGANISM: Artificial Sequence
<220> FEATURE:
<223> OTHER INFORMATION: Synthetic sequence

<400> SEQUENCE: 12
ctctctccat gagag                                                        15

<210> SEQ ID NO 13
<211> LENGTH: 15
<212> TYPE: DNA
<213> ORGANISM: Artificial Sequence
<220> FEATURE:
<223> OTHER INFORMATION: Synthetic sequence

<400> SEQUENCE: 13
tgggtctcgc accca                                                        15

<210> SEQ ID NO 14
<211> LENGTH: 25
<212> TYPE: DNA
<213> ORGANISM: Artificial Sequence
<220> FEATURE:
<223> OTHER INFORMATION: Synthetic sequence

<400> SEQUENCE: 14
ccgagaagtt aagacctatg ctcgg                                             25

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
atggagagag tgggtgcgag                                                   20

<210> SEQ ID NO 16
<211> LENGTH: 38
<212> TYPE: RNA
<213> ORGANISM: Artificial Sequence
<220> FEATURE:
<223> OTHER INFORMATION: Synthetic construct

<400> SEQUENCE: 16
ggaucccgac uggcgagagc cagguaacga auggaucc                               38

<210> SEQ ID NO 17
<211> LENGTH: 19

```
<212> TYPE: RNA
<213> ORGANISM: Artificial Sequence
<220> FEATURE:
<223> OTHER INFORMATION: Synthetic construct

<400> SEQUENCE: 17
gcacccauuu cccgacugg                                              19

<210> SEQ ID NO 18
<211> LENGTH: 14
<212> TYPE: DNA
<213> ORGANISM: Artificial Sequence
<220> FEATURE:
<223> OTHER INFORMATION: Synthetic construct

<400> SEQUENCE: 18
gagagagtgg gtgc                                                   14

<210> SEQ ID NO 19
<211> LENGTH: 25
<212> TYPE: RNA
<213> ORGANISM: Artificial Sequence
<220> FEATURE:
<223> OTHER INFORMATION: Synthetic sequence

<400> SEQUENCE: 19
ccagguaacg aauggauucu cucuc                                       25
```

MICROARRAYS OF BINARY NUCLEIC ACID PROBES FOR DETECTING NUCLEIC ACID ANALYTES

STATEMENT OF GOVERNMENTAL INTEREST

This research was made with US government NIH, NHGRI R21_HG004060.

BACKGROUND OF THE INVENTION

1. Field of the Invention

The present invention relates to binary nucleic acid probes arranged on a microarray for nucleic acid analysis.

2. Description of the Related Art

The growing importance of sensitive and selective determination of nucleic acids is associated with detection of viruses, microorganisms, and genetic traits that are not only of clinical significance, but also of environmental, defense, veterinary and agricultural importance. Simple and sensitive sequence-specific methods of nucleic acid analysis are needed, for example, for the rapid diagnosis of infection and genetic diseases, genome study, mRNA monitoring in living cells, for environmental and forensic applications. Binary nucleic acid probes that have extraordinary selectivity and specificity, can be used at ambient temperature, are low cost, and adaptable for fluorescent or visual detection have been described. However there is still a need for microarrays of the binary probes that enable high throughput analysis of a complex mixture of nucleic acids and for new binary probes for detecting them.

BRIEF DESCRIPTION OF THE DRAWINGS

The present invention is illustrated by way of example, and not by way of limitation, in the figures of the accompanying drawings and in which like reference numerals refer to similar elements.

FIG. 11 Is a schematic of a microarray of non-enzymatic binary probes that selectively hybridize to a reporter oligonucleotide (RO) when the analyte-binding arms of the probe hybridize to the target analyte.

DEFINITIONS

Figure 1:
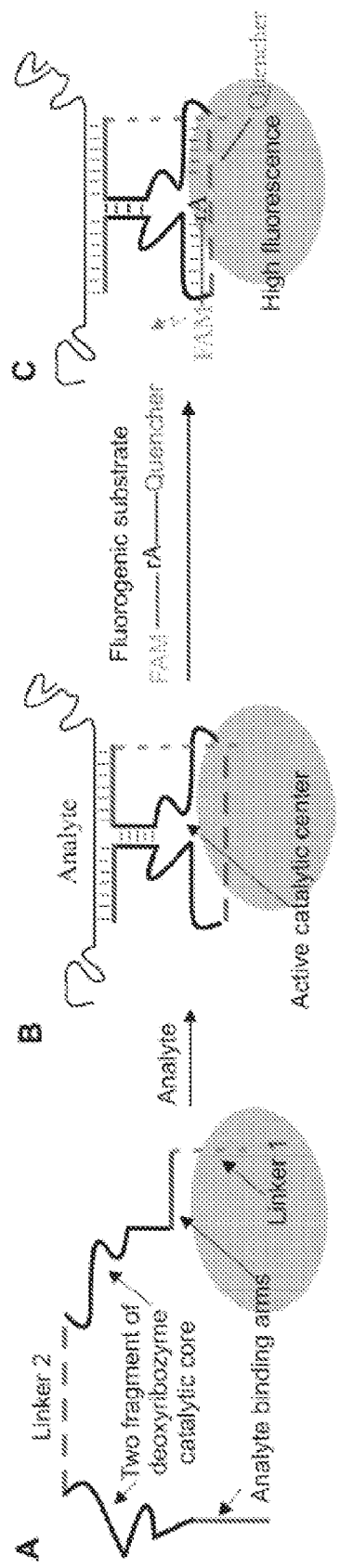
FIG. 1. A: Variant of deoxyribozyme array in which the two oligonucleotide strands of the binary probe are joined via Linker 2 (cyan) to make a single stranded binary probe complex that is immobilized on a solid support at a particular site on the microarray via another linker. This binary probe complex contains two fragments of deoxyribozyme catalytic core (black) connected via Linker 2. The single DNA strand making up the binary probe complex is in turn attached to the solid support via Linker 1 (orange). B: Active deoxyribozyme is formed in the presence of DNA analyte that hybridizes to the analyte-binding arms on the binary probe complex. C: The deoxyribozyme cleaves a fluorogenic substrate generating a fluorescent signal.

A binary nucleic acid probe is a probe that is made of two synthetic, non-naturally occurring, antiparallel oligonucleotide strands of DNA or RNA, or combinations or analogues thereof that act synergistically to detect a particular target nucleic acid analyte in a complex sample. Each strand of the probe has an analyte-binding arm (ABA) that is complementary to a portion of the particular target analyte. When the ABA hybridize to the target, causing the two strands of the probe to self assemble to generate a detectable signal indicating the presence of the target analyte in the sample. In the absence of a nucleic acid analyte, the strands are dissociated and no signal is generated. As used herein, the term "physiologic conditions" is meant to suggest reaction conditions emulating those found in mammalian organisms, particularly humans. While variables such as temperature, availability of cations, and pH ranges may vary. "Physiologic conditions" generally mean a temperature of about 35-40° C., with 37° C. being particularly preferred, and a pH of about 7.0-8.0, with 7.5 being particularly preferred. The conditions also include the availability of cations, preferably divalent and/or monovalent cations, with a concentration of about 2-15 mM $Mg^{2+}$ and 0 1.0 M $Na^+$ being particularly preferred.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a "nucleoside". When the nucleoside contains a phosphate group bonded to the 3' or 5' position of the pentose, it is referred to as a nucleotide. A sequence of nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

In various embodiments, the binary probe of the present invention may combine one or more modifications or mutations including additions, deletions, and substitutions. These mutations may, for example, change the length of, or alter the nucleotide sequence of, a loop, a spacer region or a recognition sequence (or domain). Modification or mutation of the recognition site via well-known methods allows one to alter the sequence specificity of an enzymatic nucleic acid molecule. The oligonucleotide strands of the probe may contain one or more substitutions such as analogues, derivatives, modified or altered bases, ribonucleotides, alterations of the sugar or phosphate backbone, or any combination of these, well known to those skilled in the art As used herein, the terms "deoxyribozyme" and "ribozyme" are used to describe a DNA or RNA-containing nucleic acid that is capable of functioning as an enzyme. In the present disclosure, the term "deoxyribozyme" and "ribozyme" includes endoribonucleases and endodeoxyribonucleases, although deoxyribozymes/ribozymes with endoribonuclease activity are particularly preferred. Other terms used interchangeably with deoxyribozyme/ribozyme herein are "enzymatic DNA/RNA molecule", "DNAzyme/ RNAzyme", or "catalytic DNA/RNA molecule", which terms should all be understood to include enzymatically active portions thereof, whether they are produced synthetically or derived from organisms or other sources. The basic probe has several distinct regions on each strand: an analyte-binding arm flanked by a flexible linker that is flanked by a molecular beacon-binding arm that binds to a molecular beacon to indicate that the analyte has been detected. These probes are called "binary" because the two parts of the probe act synergistically and the detection event occurs only when both strands are hybridized to the analyte. In the absence of a nucleic acid analyte, the strands are dissociated and the probe does not detect the presence of the analyte.

(Deoxy)ribozymes or DNA/RNA enzymes or catalytic DNA or RNA are DNA or RNA molecules with catalytic action. These molecules can bind one or more than one substrates and chemically transform them.

An aptamer is an RNA or DNA molecular that can specifically bind a specific target molecule. Aptamers are usually created by selecting them from a large random sequence pool.

Reporter Oligonucleotide means an oligonucleotide to which a reporter molecule is linked, such as a gold nanoparticle, fluorescent molecule, quantum dot or any reporter that can be detected. In some embodiments the nonenzymatic probes have a reporter oligonucleotide-binding arm that is complementary to and hybridizes to the RO thereby generating a detectable signal. The reporter molecule is any molecule that can be detected by optical, electrical or magneto electrical means.

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G (as well as U) may occasionally participate in base pairings. Nucleotides that normally pair up when DNA or RNA adopts a double stranded configuration may also be referred to herein as "complementary bases".

"Complementary nucleotide sequence" here generally refers to a sequence of nucleotides in a single-stranded molecule or segment of DNA or RNA that is sufficiently complementary to that on another single oligonucleotide strand to specifically hybridize to it with consequent hydrogen bonding. Where single nucleotide polymorphisms are the target for detection, then the complementarity between the analyte and analyte-binding arm on the binary probes should be exact, 100%. If less selectivity is required, then routine experimentation will determine the level of complementarity that provides the desired result.

"Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different or unusual sugars (i.e. sugars other than the "usual" pentose), or a combination of the two. Nucleotide analogs of DNA or RNA can be used to make binary probes. Examples of nucleotide analogs useful according to the present invention include those listed in the approved listing of modified bases at 37 CFR .sctn.1.822 (which is incorporated herein by reference). Other useful analogs include those described in published international application no. WO 92/20823 (the disclosures of which are incorporated herein by reference), or analogs made according to the methods disclosed therein.

"Oligonucleotide or polynucleotide" generally refers to a polymer of single-stranded nucleotides. As used herein, "oligonucleotide" and its grammatical equivalents will include the full range of nucleic acids. An oligonucleotide will typically refer to a nucleic acid molecule comprised of a linear strand of deoxy- and ribonucleotides.

A nucleic acid microarray is a multiplex technology used in molecular biology that consists of an arrayed series of up to thousands of microscopic spots of DNA or RNA or DNA/RNA chimeric oligonucleotides, called features, each containing picomoles of a specific nucleic acid sequence.

DETAILED DESCRIPTION

It is to be understood at the outset, that the figures and examples provided herein are to exemplify, and not to limit the invention and its various embodiments.

The present invention is directed to microarrays of binary nucleic acid probes for the detection of one or a plurality of nucleic acid analytes in a complex sample in a single high throughput assay with extraordinary specificity under physiologic conditions. Any binary nucleic acid probes that generate a detectable signal when bound to analyte are suitable for use in the microarrays, including binary deoxyribozyme or ribozyme probes; nonenzymatic binary probes for fluorescent detection, nonenzymatic binary dye-binding probes, and binary split enzyme peroxidase probes for visual detection of nucleic acids. Certain embodiments are also directed to non nonenzymatic binary probes that bind to reporter oligonucleotides:

Binary probes and the microarrays to which they are bound have the following advantages in comparison to the conventional microarrays of liner DNA probes. (i) improved selectivity of SNP detection (low level of false positive signals), (ii) avoid the need for the precise temperature control during hybridization as the reactions can be conducted at ambient temperatures, (iii) improved sensitivity due to catalytic amplification of the positive signal, (iv) simplified readout procedure: in some formats the signal may be detected by naked eye and/or by a conventional scanner, and (v) low cost: there will be no requirement for target labeling; the probes are affordable synthetic oligodeoxyribonucleotides.

Binary nucleic acid probes have two synthetic, non-naturally occurring, antiparallel oligonucleotide strands made of DNA or RNA, and combinations or analogues thereof that act synergistically to detect a target nucleic acid analyte in a complex sample. Each strand of the probe has an analyte-binding arm (ABA) that is complementary to and hybridizes with a portion of a specific target analyte, causing the two strands of the probe to self assemble to generate a detectable signal indicating the presence of the target analyte in the sample. In the absence of a nucleic acid analyte, the strands are dissociated and no signal is generated.

Any binary probe can be used in the microarrays. In some embodiments the microarray includes binary enzymatic nucleic acid probe, wherein each strand of the probe has part of the catalytic core of the enzyme that is reconstituted when the ABA on the two strands of the probe hybridize to the analyte, restoring the catalytic activity of the enzyme and enabling it to bind to a substrate through substrate-binding arms on each strand and cleave the substrate, which in turn generates a detectable signal, such as a fluorescent signal or a color change (in the case of peroxidase). In some embodiments the microarray is designed so that a single substrate is adequate for the plurality of different probes immobilized on a microarray. In other embodiments more than one substrate may be used depending on how the binary probes are customized. In some embodiments a unique substrate may be needed to detect each of several different target analytes. PCT Application PCT/US07/61583, Kolpashchikov D. M. (2007) ChemBioChem, 8, 2039-2042; Todd et al., U.S. Ser. No. 11/544,926 (20070231810), and in E. Mokany, et al., J. Am. Chem. Soc. 2010, 132 (3), pp 1051-1059.

In some embodiments the microarray includes binary nonenzymatic probes, designed to selectively bind to a molecular beacon or a dye (through molecular beacon-binding arms or dye-binding arms, respectively) or to a reporter oligonucleotide bound to any detectable molecule (such as a quantum dot, gold nanoparticle is bound) thereby generating a detectable signal when the analyte-binding arms on each strand hybridize to the particular target nucleic acid analyte. PCT Application PCT/US2007/065744, Kolpashchikov D. M. (2006) JACS, 128, 10625-10628; and Kolpashchikov D. M. (2005) JACS, 127, 12442-12443.

In other embodiments the microarray includes binary probes that have peroxidase-like activity that produce a visible signal when complexed to the target analyte. When both of the analyte-binding arms bind a target analyte, the two strands of the probe form a hemin-binding complex. Hemin has peroxidase activity that can be visualized by adding the appropriate substrate to generate a colored product indicating that the analyte has been detected. U.S. Provisional application 61/117,081, PCT Application PCT/US09/65341 and Kolpashchikov D. M. (2008) JACS, 130, 2934-2935.

The binary probes are sensitive to even a single nucleotide mismatch, which destabilizes the probe preventing the two halves of the probe from hybridizing to the analyte to generate a signal. As was reported earlier, the binary probes provide unprecedented selective recognition of 20 nucleotide long targets (that can be part of an even longer nucleotide) at room temperature, thus avoiding the need for the precise temperature control for SNP typing. The array of binary probes is an extremely efficient tool for pathogen and SNP analysis and may revolutionize DNA microarray technique. Sequence variations capable of detection by the microarrays of the present invention include, but are not limited to, additions, deletions, substitutions, conversions, duplications, translocations, frame-shift sequence variants, nonsense sequence variants, or any combination thereof. Reactions can be performed over a wide range of temperatures, as long as the probes function as intended to generate the signal upon hybridization to analyte. Because the probes discriminate between fully matched nucleic acid sequences and those containing mismatches, they can be used for the detection, identification and quantification of methylated nucleic acid. Abnormal methylation pattern occur frequently in association with diseases such as cancer, diabetes, autoimmune diseases, and psychiatric disorders.

Immobilizing Binary Probes on a Microarray

There are several ways in which the binary probe microarrays can be created. In certain embodiments either one or both strands of the binary probe are immobilized on a solid support. In embodiments where both strands are immobilized, the two strands of the binary probe are linked to one another through a flexible linker that permits each strand to hybridize to the target analyte thereby generating a detectable signal. The linker joining two strands of a binary probe is labeled "linker 2" in the figures. When the two strands are linked, the resulting molecule is herein referred to as a "binary probe complex" and microarrays on which such complexes are immobilized are referred to as "binary probe complex microarrays.

In one embodiment, the two strands of the probe are bound to each other via an interstrand linker to make the binary probe complex. In another embodiment the binary probe complex is formed by joining the ends of the two strands opposite the analyte-binding arm (ABA) through an intrastrand linker to form a single oligonucleotide that comprises both strands, leaving the ABA are free to bind to analyte as shown in FIG. 1. The plurality of binary probe complexes are immobilized at a particular spot on the microarray through another tethering linker (labeled "linker 1" in the figures) that can bind to any location on the complex as long as it does not interfere with target binding or signal generation. The tethering linker is itself covalently bound to the array; many such linkers are well known in the art. Both linkers are preferably flexible linkers that permit the two halves of the probe to form a double helix when bound to analyte.

An embodiment in which the microarray features are made by joining the two strands of the binary enzymatic probe to one another via an intrastrand linker to make a single oligonucleotide or binary, probe complex. In the example shown in FIG. 1A a linker (Linker 1) joins the two strands through the substrate-binding arms on each strand, leaving the analyte-binding arms free to bind to the analyte. In the absence of a nucleic acid analyte the catalytic core remains deactivated due to the weak interactions between the two halves. Hybridization of each analyte-binding arm of the probe to a target analyte stabilizes the structure of the core (FIG. 1B) thereby forming an active enzyme. If a fluorogenic substrate is added that is complementary to and hybridizes with the substrate-binding arm on each strand, the enzyme will cleave the fluorogenic substrate. The quencher will dissociate in solution and the fluorophore will emit high fluorescence (FIG. 1C).

Figure 2:
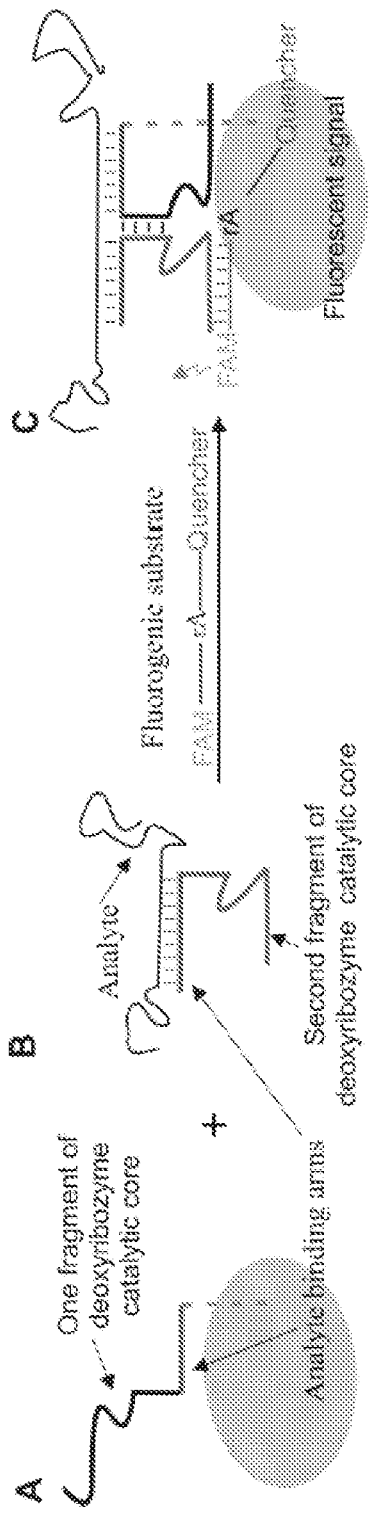
FIG. 2. Array of binary deoxyribozymes for fluorescent detection of nucleic acids in which A: each feature has one strand ("the first strand") of a binary deoxyribozyme probe immobilized on a solid support via a linker (red dashed line). The first strand includes a fragment of the deoxyribozyme catalytic core (black). B: The second strand of the binary deoxyribozyme probe that contains the other half of the catalytic core (blue) is supplied separately. In this example the second strand is mixed with the target analyte that binds to the analyte-binding arm (green) forming a strand/analyte hybrid. The hybrid is then added to the microarray. The immobilized first strand binds the analyte causing the two halves of the binary probe to hybridize reforming the active catalytic core. C: The active DNAzyme cleaves a fluorogenic substrate and increases the fluorescence of the feature.

Alternatively, the microarray feature can be made by immobilizing only one strand of the binary enzymatic probe (half of the probe) on the solid support. In the example shown in FIG. 2A a linker (Linker 1) is bound to the free end of the analyte-binding arm on a first oligonucleotide strand of a binary deoxyribozyme probe. The second oligonucleotide strand of the probe is provided separately. In one embodiment the second strand of the probe is mixed with the target analyte under conditions that permit the analyte to hybridize to the analyte-binding arm on the second strand to form an analyte/strand hybrid as is shown in FIG. 2B. The hybrid is then added to the microarray under conditions that permit a portion of the target analyte to bind to the analyte-binding arm on the first strand that is immobilized on the solid support, thereby forming a complex that activates the enzyme. In another embodiment the analyte can be added to the microarray onto which the first strand is immobilized either before, together with or after adding the second strand. The appropriate substrate is added to the mixture at any time. The substrate then binds to the substrate-binding arms on the first and second strand of the probe/analyte complex, and it is cleaved by the activated enzyme thereby generating a detectable signal indicating the presence of the target analyte and its binding to the probe. FIG. 2C.

Routine experimentation will determine the optimum conditions and timing for adding the various components necessary for detecting the analyte in the complex sample. Any technique can be used as long as it permits the specific binding of analyte to the ABA and generation of a detectable signal.

In another embodiment of the microarray the molecule generating the detectable signal is bound to the support and the binary probe is added separately, either as two free strands, or as a binary probe complex wherein the two strands are linked. In the case of an enzymatic probe, the enzyme is activated only when the two strands bind to the target analyte reconstituting the catalytic core. The activated enzyme then cleaves the bound substrate generating a signal localized to the corresponding feature. In a preferred embodiment the fluorescent end of the substrate remains immobilized on the microarray and the quencher is released into solution upon cleavage. If the probe is nonenzymatic, the bound molecule can be a dye or molecular beacon that generates a signal only when the respective dye-binding or molecular beacon-binding arms hybridize to target analyte.

In preferred embodiments a microarray is provided on which a plurality of binary probe complexes and/or single strands of the plurality of binary probes that detect a plurality of nucleic acid analytes are immobilized at different sites on a solid support to create features. A single microarray can include features that comprise 1.) binary probe complexes in which the two strands are linked at an interstrand site, or 2.) binary probe complexes in which the two strands are linked at an intrastrand site to form a single long oligonucleotide, or 3.) only one strand of a probe immobilized to create a feature wherein the other strand is added separately, or 4.) the signal-generating molecule is immobilized on the support, or 5.) combinations of these. Moreover the binary probes themselves can be of any type, enzymatic or nonenzymatic. Since hybridization can be accomplished at physiologic conditions it is possible to put different types of binary probes on the same microarray, for example, mixing enzymatic and nonenzymatic probes, or different types of each. The target nucleic acid analyte is added to the microrray under any conditions that permit it to selectively hybridize with the corresponding analyte-binding arms on the respective binary probe, thereby permitting the two strands of the probe to hybridize which generates a detectable signal indicating analyte-binding.

In standard microarrays, the probes are attached to a solid surface by a covalent bond to a chemical matrix (via epoxy-silane, amino-silane, lysine, polyacrylamide or others) or the solid surface can be glass, a silicon or an organic polymer chip. Many types of solid supports/surfaces are known in the art. In certain preferred embodiments, the support can be a plastic material, such as plastic beads or wafers, or that of the well or tube in which a particular assay is conducted. The immobilized probes complex creates what is called a feature on the microarray. Any method or linker that tethers a strand of the binary probe to the support can be used, including any methods that may involve noncovalent linkages, as long as the strand remains immobilized during the assay. Embodiments of the present invention encompassing an insoluble support in the form of an array or microarray called a "chip," typically comprise a plurality of probes that are positioned upon the chip by any suitable method known in the art, for example, by pipette, ink-jet printing, contact printing or photolithography. The microarray/chip may have one or more features that may be spaced apart at a uniform or a variable distance, or a combination thereof. In some embodiments, the features may be positioned randomly, with the respective location of each element then determined. The size and shape of the features will vary according to the intended use, and different sized and shaped features may be combined into a single microarray/chip. The surface of the microarray/chip may be substantially planar or may have uneven topography such as depressions or protuberances. The features may be positioned either into the depressions or onto the protuberances. Such depressions may provide a reservoir for solutions into which the features are immersed, or they may facilitate drying of the elements. For example, the features may be placed in each well of a 96 well plate. In some embodiments, the microarray/chip may include unique identifiers such as indicia, radio frequency tags, integrated devices such as microprocessors, barcodes or other markings in order to identify each of the elements. The unique identifiers may additionally or alternatively comprise the depressions or protuberances on the surface of the array. The unique identifiers can provide for correct orientation or identification of the microarray/chip and they may be read directly by a data capture device or by an optical scanner or detector.

Binary Probe Structure

Figure 6:
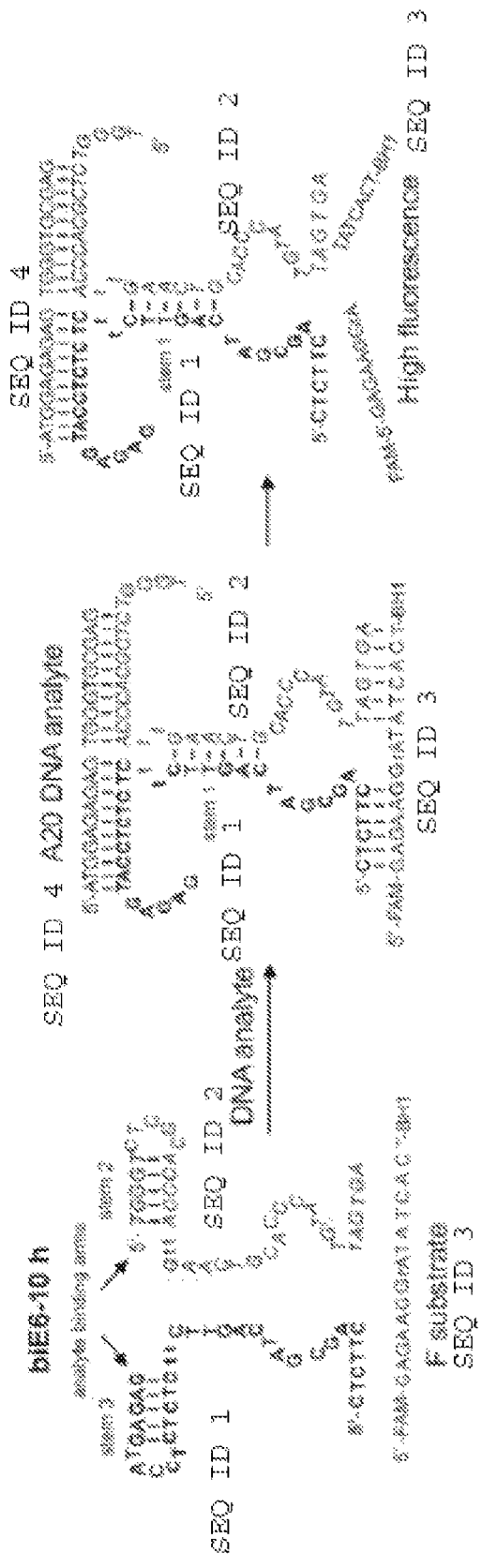
FIG. 6 shows the structure of the two strands of the biE6-10h binary enzymatic probe which in this embodiment has a structure stabilization arm attached to each analyte-binding arm that form a stem loop structure in the absence of analyte. In the left panel the two strands are separate. The sequence of a fluorescent substrate for the enzyme is shown. In the presence of analyte, the stem loops open, the analyte-binding arms bind to the analyte, the probe-binding arms hybridize reconstituting the catalytic core of the deoxyribozyme, and the substrate-binding arms bind the fluorescent substrate (Center Panel). In the right panel, the activated enzyme hydrolyzes the substrate generating a detectable fluorescent substrate.
Figure 7:
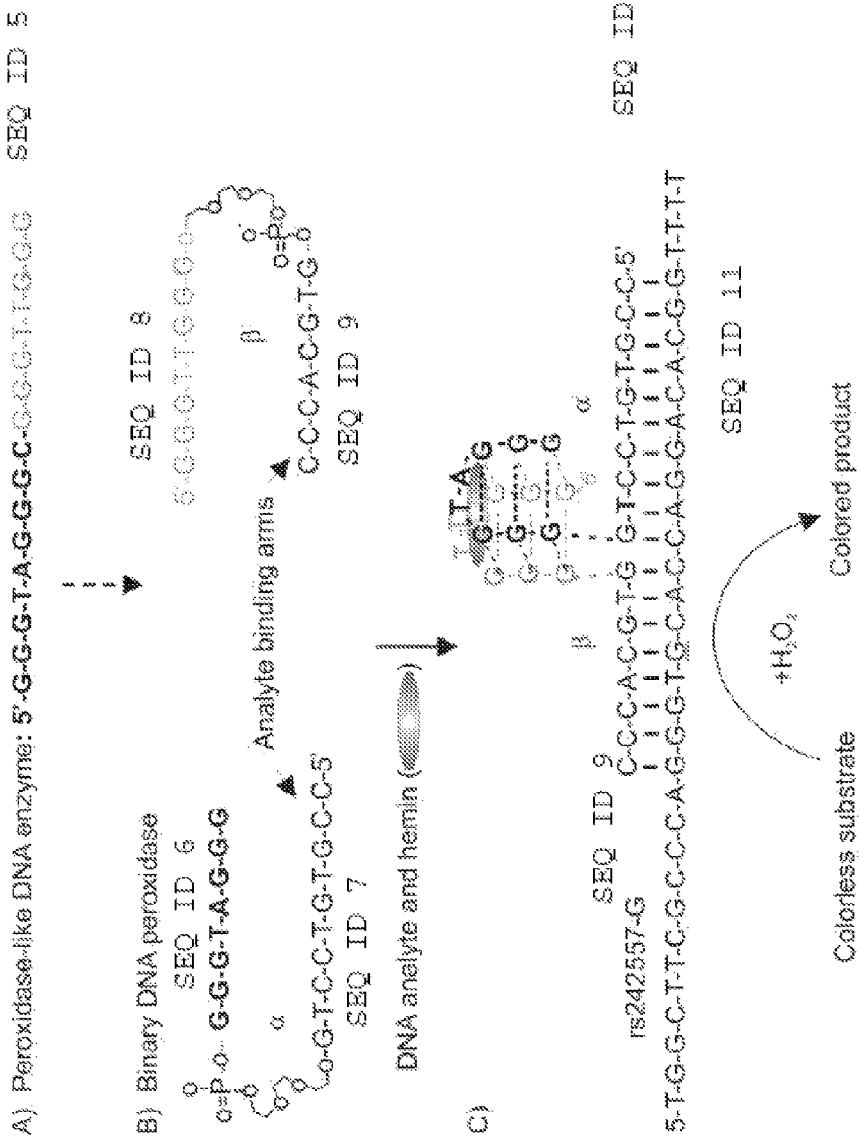
FIG. 7 Design of an embodiment of a binary DNA peroxidase for SNP analysis. A: Parent peroxidase-like DNA enzyme. B: Binary DNA peroxidase probe. C: The probe forms active peroxidase upon hybridizing to the abutting positions of the analyte. The enzyme catalyzes oxidation of a colorless substrate to colored products. The triethylenglycol linkers are shown as dashed lines in panel C. The SNP site in the analyte sequence is underlined.

The arms of any of the binary probes (such as the substrate-, dye- or MB-binding arms, catalytic core and analyte-binding arms) are "linked" to one another typically through phosphodiester bonds between the nucleotides at the ends of each respective arm, without adding additional linkers. However, in some embodiments one or more separate linker molecules are added between one or more arms of the probe. Any separate linkers added to the probe strands to join the parts or arms of the probe on each strand to one another can be used as long as they are flexible enough to permit the probe to generate a detectable signal when the ABA bind to the analyte. In some cases the ABA will form a double or triple helix when bound to analyte. In one example embodiment the ABA are homopyrimidine (alternating C and T, such as CCCTTTC-CCCCCCTTTT) or homopurine (such as GGGAAAGGGG-GAGAGA) sequences. Flexible linkers are generally preferred. Binary RNA probes also form double helices. In certain embodiments the added linkers are nucleic acids, typically from about 0 to about 3 nucleotides long, though longer linkers can be used (FIG. 6; "tt" is an added dinucleotide linker), or a non-nucleotide linker such as triethylene glycol can be used (FIG. 7). Hexa-ethyleneglycol provided for example by Integrated DNA Technologies (Coralville, Iowa, USA) can also be used although this would substantially increase the cost of the probe. The length and sequence of the linkers between the various arms can also vary. Due to steric considerations pyrimidines are favored over purines when used as linker bases. Therefore in certain embodiments probes such as T, TT, TTT, C, CC, CCC linkers are preferred. In some embodiments the linker can be a short nucleotide such as a dinucleotide uracil bridge. Routine experimentation will determine the optimum probe design providing the highest specificity and in the case of enzymatic probes, the highest rate of substrate cleavage in the presence of a DNA or RNA analyte with the lowest background. Additional examples of flexible linkers are demonstrated in Example 4. It is not necessary that the linkers on each strand be identical, as long as they permit the ABA to bind to the analyte and generate the detectable signal. The length and sequence of the various components of the binary nonenzymatic probes can be varied as is described in PCT Serial No. PCT/US07/61583, PCT/US2007/065744, and 61/117,081 to customize the probe for a particular analyte and optimize the reactions.

All of the binary probes for use in the present invention can be made of DNA, RNA, 2'-O-methyl RNA, locked nucleic acids (LNA), or peptide nucleic acids (PNA) or any other nucleic acid analogues that can form double and triple helixes with nucleic acids or they can be a chimera. Likewise the analyte can be DNA, RNA or a chimera. Since DNA-RNA and DNA-DNA hybrids have different structural parameters, the binary constructions should be customized for RNA in order to obtain highly specific and sensitive recognition of RNA targets. DNA probes have an advantage over RNA probes when the analyte is DNA because DNA-DNA duplexes are typically less stable than RNA-DNA duplexes and are therefore more sensitive to SNPs. DNA probes are cheaper also to synthesize and they are more stable to degradation in solution. In those embodiments where the probes are made of RNA oligoribonucleotides, U is substituted for T; otherwise the structures are the same.

Typically only two short DNA, RNA, chimeric or oligonucleotides need to be synthesized for each type of probe. The specific analyte-binding arms for each different probe have to be customized. Standard desalting provides sufficient purity for the oligonucleotides of such lengths. All other components of the probe, such as the substrates for enzymatic probes or double labeled fluorescent molecular beacons, or the dyes are universal.

In general, for all types of binary probes, analyte-binding arms of 10 nucleotides are preferred because a combined length of 20 nucleotides will cover any unique sequence in the genome. It is important to note, that the analyte itself can be of any length from 12-40, to many thousand nucleotides. Additional changes that may increase the selectivity of the probe include shortening the analyte, for example from 20 to 12 nucleotides, or increasing the reaction temperature. Since the oligonucleotide strands of the binary probe are simple nucleotide sequences they can be made to order by various existing companies such as Integrated DNA Technologies (Coralville, Iowa, USA).

The basic structure of all of the binary probes can be modified. One modification includes adding a stem or probe-binding arm, for example between the substrate-binding arm and the catalytic core (or between the catalytic core and the ABA) on each strand of deoxyribozyme or ribozyme probes. The probe-binding arm provides a stem-loop type structure to the probe and can add additional structural stability that in some cases enhance catalytic activity.

In another embodiment a nucleotide fragment of from about 0-40 nucleotides in length (preferably 1-10) called a structure stabilization arm (SSA) is added to the free end of the analyte-binding arm on each strand of a probe to increase sensitivity and stability of the probes. The added sequences in the SSA are complementary to all or part of the analyte-binding arm. When the complementary sequences in the SSA hybridize to the corresponding sequences in the analyte-binding arm, a stem-loop is formed. The formation of stem-loops represents a conformational constraint that further increases the sensitivity of the binary DNA or RNA probes. SSA can also be added to the free end of the hemin-binding arm on peroxidase-like probes if they do not interfere with g-complex formation. When the strands of the probe are present free in solution, i.e., not hybridized to analyte, each dissociated strand of the probe is stabilized by complementary base pairing to itself via the stem loop in the analyte-binding arms. This self-complementary pairing results in a "hairpin loop" structure for the individual strands, which stabilizes the oligonucleotide strands and increases sensitivity. Certain preferred embodiments of the invention are therefore directed to the binary oligonucleotide probes where each strand of the probe forms a stem loop structure when the strand is not hybridized to analyte. When analytes are 16 nucleotides long or shorter, adding stem-loops to the analyte-binding arms may not be helpful. The size of the SSA will depend on the size of the analyte and the type of reporter (dye or MB), which will vary. It was discovered that sensitivity to a single mismatch or single nucleotide polymorphism in analytes 20 nucleotides long increased if each strand of the probe was designed to form a stem-loop hairpin structure when not bound to analyte.

Certain other embodiments of the invention are directed to microarrays on which truncated forms of the probes as are bound or provided in solution. An example of a truncated binary deoxyribozyme probe is a probe each strand of which has only substrate-binding arms and a portion of the catalytic core. Users can customize the other regions of the probe, adding for example ABA for any intended target analyte.

Figure 5:
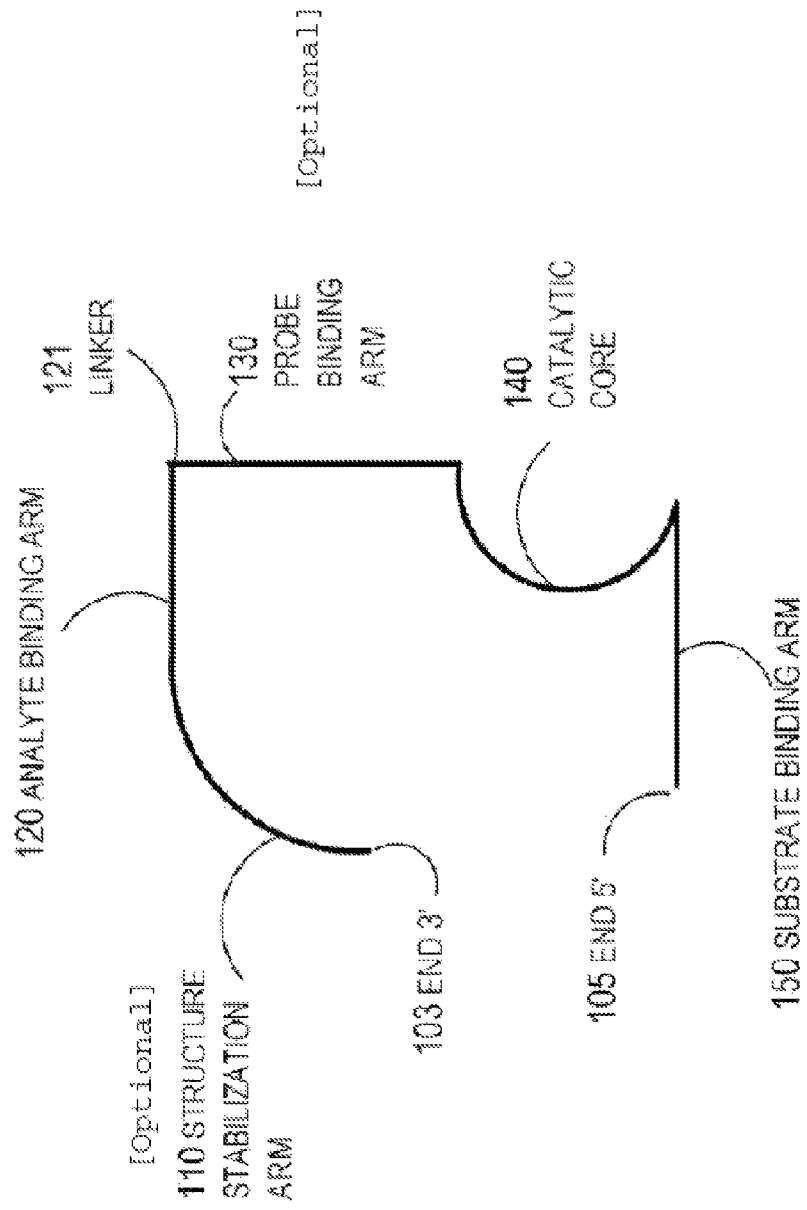
FIG. 5 is a schematic of an embodiment of one of the two oligonucleotide strands of a binary deoxyribozyme probe.

Binary enzymatic probes include any binary deoxyribozyme, ribozyme or chimeric probes. Each oligonucleotide strand of a binary enzymatic probe has a substrate-binding arm (that binds the enzyme substrate such as a fluorescent substrate), (roughly) half of the catalytic core of the enzyme and an analyte-binding arm. In some embodiments the probe includes an optional probe-binding arm that lends structural stability to the probe and may improve enzymatic activity. (FIG. 5). In some embodiments, the oligonucleotide strands of binary enzymatic and nonenzymatic probes have optional structure stabilization arms that are linked to the analyte-binding arms, and that provide structural stability and minimize nonspecific binding to analyte. A large variety of reporter substrates including fluorophores and quenchers can be used in enzymatic probes (such as FAM, TET, TAMRA and others known in the art, and quenchers (such as Dabcyl, TAMRA, Iowa Black™, Black Hole Quencher®-1, Black Hole Quencher®-2) are commercially available (IDT Inc.).

Figure 3:
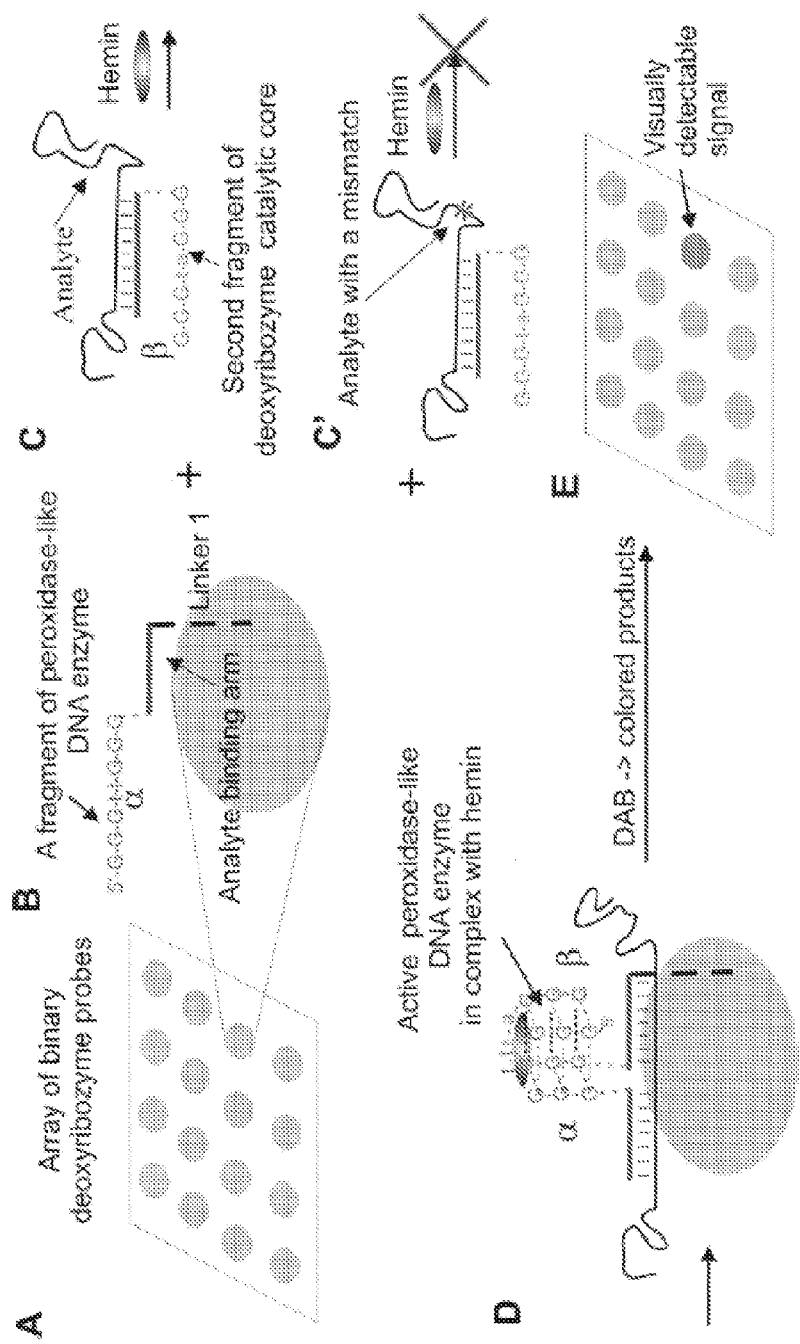
FIG. 3 Scheme of the array of binary oligonucleotide peroxidase probes for visual (colorimetric) detection of nucleic acids. A: A chip (solid support) contains an array of oligonucleotides. B: As in FIG. 2, the first strand of the probe having a fragment alpha includes the catalytic core of the peroxidase-like DNA enzyme(blue) and analyte-binding arm (green line) is attached to the solid support via Linker 1 (dashed line). C: In this example the second strand that has the second fragment of the deoxyribozyme catalytic core (beta, orange) provided separately, hybridizes to the analyte in solution. C': In this example the second strand of the deoxyribozyme probe hybridizes with analyte containing a single-base mismatch. D: Catalytically active peroxidase-like DNA enzyme is formed only in C where the analyte-binding arms are fully complementary to the analyte. The reformed peroxidase catalytic core forms a G-quadruplex that binds hemin from the solution and decomposes hydrogen peroxide; the decomposition products convert a colorless substrate such as DAB (3,3'-diaminobenzidine) to a water insoluble colored product that can be detected. E: The water-insoluble product forms brown spots on the array.

An example of a microarray feature in which the binary probe is a peroxidase DNA enzyme is shown in FIG. 3. Provisional application 61/117081, PCT Application PCT/US09/65341 and Kolpashchikov D. M. (2008) JACS, 130, 2934-2935. In this embodiment, each strand peroxidase probe has a customized fragment that is complementary to a selected target nucleic acid analyte (analyte-binding arm), and a customized fragment complementary to hemin (hemin-binding arms). While the ABA on a peroxidase-like probe can be DNA, RNA or chimeras, the hemin-binding arms are only made of DNA. In the embodiment shown in FIG. 7, analyte- and hemin-binding arms are connected to each other by added non-nucleotide linker molecules. When both of the analyte-binding arms bind a target analyte, the two strands of the probe bind hemin which has peroxidase activity that can be visualized by adding the appropriate substrate to generate a colored product indicating that the analyte has been detected.

In the example shown in FIG. 3, each half of the binary peroxidase-like probe contains a fragment (alpha and beta) of the catalytic core of the DNA peroxidase enzyme, and only one strand is immobilized on the surface of the array by linker 1 (FIG. 3B). This fragment is unable to form catalytic complex with hemin until the ABA on both the first second strands hybridize to target analyte. In this embodiment, the second strand of the probe is mixed with the target analyte in solution permitting the analyte to bind to the analyte-binding arm on the second strand to form a hybrid (FIG. 3C). The second strand/analyte hybrid is then mixed/incubated with the array under conditions that permit the ABA on the immobilized first strand to bind to the target analyte, thereby bringing the two halves of the probe together to form a hemin-binding G-quadruplex from the combined alpha and beta fragments. (FIG. 3D) Hemin catalyzes degradation of hydrogen peroxide and the products of peroxidase degradation in turn oxidize a number of different substrates including DAB (3,3'-diaminobenzidine) and 2,2'-azino-bis(3-ethylbenzthiazoline-6-sulphonic acid) (ABTS). Any substrate that can be hydrolyzed by peroxidase can be used. The substrate oxidation products are water insoluble and stain the microarray feature (brown in the case of DAB) (FIG. 3E), which can be detected either by a scanner or visually (in microscope in the case if the feature size in the range of micrometers). The active hemin-binding probe will not be formed if the analyte has even one non-complementary nucleotide, thus enabling the arrays to be used for SNP detection. If a substrate such as luminal is used as an oxidizable substrate instead of DAB, a chemiluminescent signal will be generated. The sensitivity of the probe can be increased if multiple substrate molecules cleavable by the reconstituted enzyme are added.

Different variations on the hemin-binding arm of the probe can be made. Some variations include the following. In one embodiment, the oligonucleotide hemin-binding arm on the first oligonucleotide strand includes the sequence 3' gggatggg 5, and the oligonucleotide hemin-binding arm on the second oligonucleotide strand includes 5' gggttggg 3'. In other embodiments the oligonucleotide hemin-binding arm on the first oligonucleotide strand comprises 3' ggg 5; and the oligonucleotide hemin-binding arm on the second oligonucleotide strand comprises 5' gggcgggttggg 3', or the oligonucleotide hemin-binding arm on the first oligonucleotide strand comprises 3' gggcgggatggg 5; and the oligonucleotide hemin-binding arm on the second oligonucleotide strand comprises 5' ggg 3'. See FIG. 3 and FIG. 7.

Figure 4:
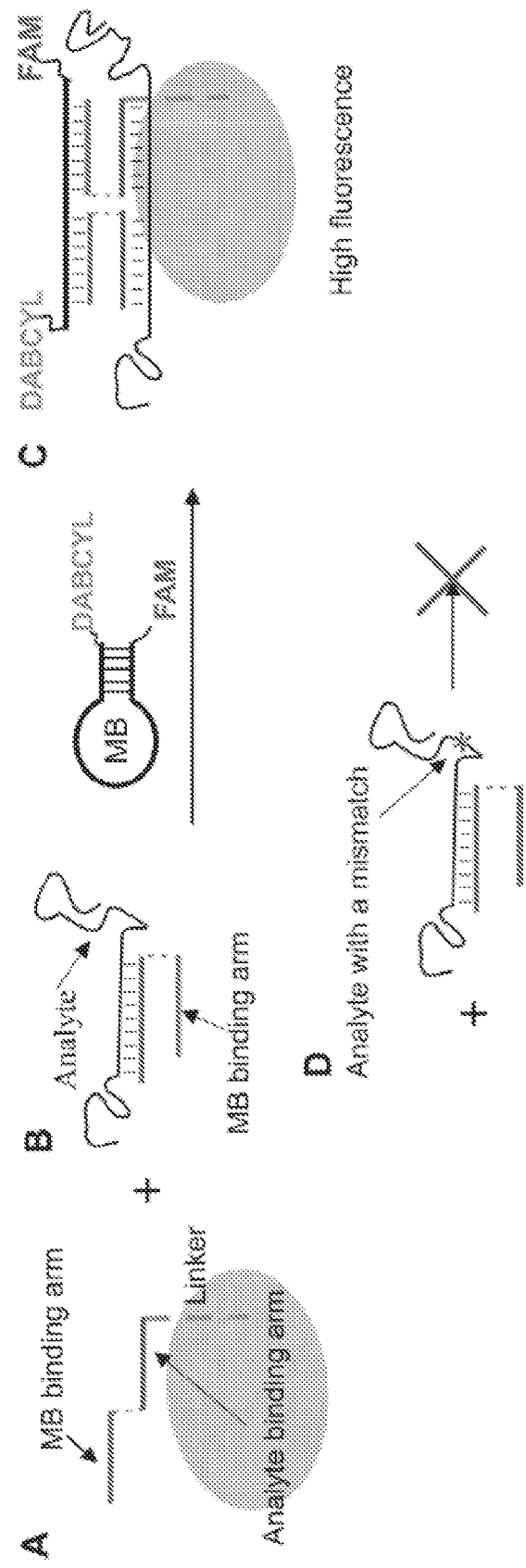
FIG. 4. Scheme of SNP analysis by an array of binary nonenzymatic DNA probes that have molecular beacon-binding arms. A: The first strand of the nonenzymatic binary probe is immobilized on a solid support via a linker attached to the analyte-binding arm. B: The second strand is hybridized separately with the nucleic acid analyte in solution. C: The strand/analyte hybrid is added to the microarray and the analyte-binding arm on the first strand hybridizes with the analyte, causing the two halves of the probe to hybridize that in turn causes the molecular beacon-binding arms on each strand of the binary probe to hybridize with a molecular beacon that was included in the solution to form fluorescent complex. D: The fluorescent complex is not formed if the analyte is not fully complementary to the analyte-binding arm of BDP strand.
Figure 8:
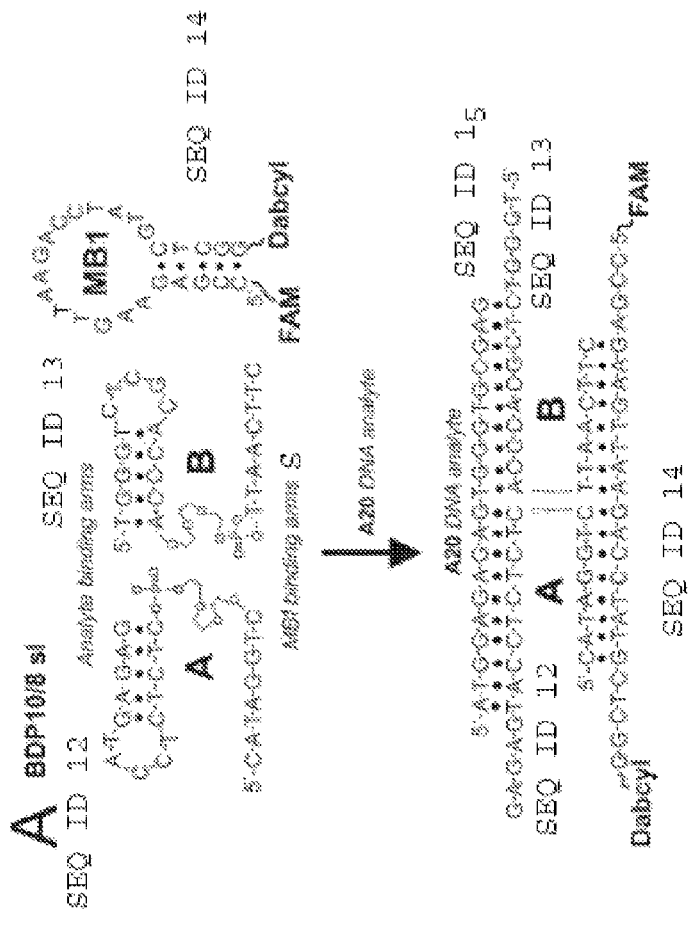
FIG. 8 Primary and secondary structure of an embodiment of a binary DNA molecular beacon-binding probe (BDPs) A: Structure of the BDP10/8sl probe in the absence (top) or presence (bottom) of A20 DNA analyte. B: Structure of strands A and B of BDP8/8 and BDP10/8. C: Structure of strands A and B of BDP10/8sl F .tul. The triethylene glycole linkers are depicted by the dashed lines on the panels A (bottom), B and C.

Nonenzymatic binary DNA probes (BDP) for use in the present invention [Kolpashchikov D. M. (2006) JACS, 128, 10625-10628] bind to molecular beacons or dyes to generate a signal. Each antiparallel strand has a MB- or dye-binding arm and an analyte-binding arm, with an optional stem between these two arms. Alternatively the MB- or dye-binding arms and the ABA on each strand are linked by an added linker such as triethylene glycol. FIG. 4 and FIG. 8. The MB- and dye-binding arms are designed to be complementary to and hybridize with nucleotide fragments or sequences in any molecular beacon or dye known in the art. A molecular beacon (MB) is a fluorophore- and a quencher-conjugated DNA or RNA hairpin. The probe can be customized for any fluorophore, including FAM, TAMRA, Dy 750, HEX™, JOE, TET™, Texas Red-X, Alexa Fluor. Dyes, Bodipy Dyes, CY Dyes, Rhodamine, dyes, WellRED Dyes, MAX, and TEX 613; and for any quencher including black hole quenchers (BHQ1, BHQ2, BHQ3), Iowa Black Quenchers, and DABCYL.

Figure 9:
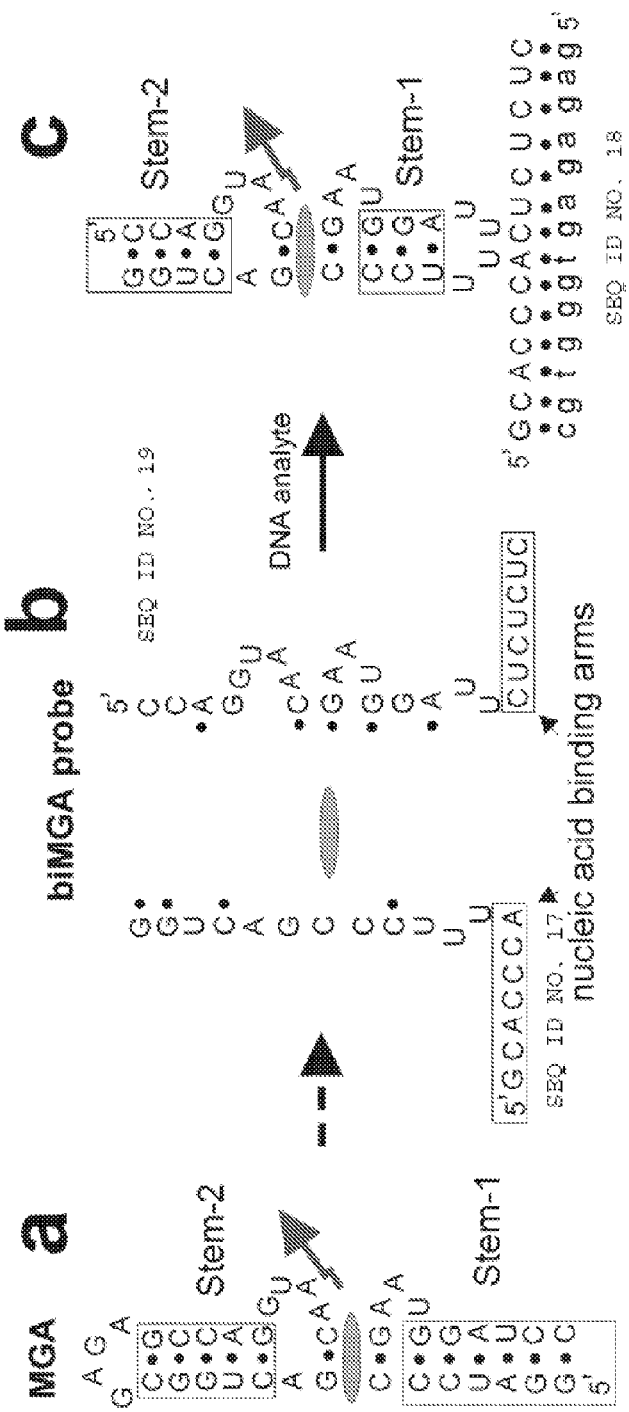
FIG. 9 (a) Structures of an embodiment of a MGA (malachite green aptamer) in complex with MG (malachite green dye). (b) The biMGA RNA probe free in solution. (c) biMGA probe bound to complementary DNA analyte. Ribonucleotides are represented in uppercase whereas deoxyribonucleotides are in lowercase.
Figure 10:
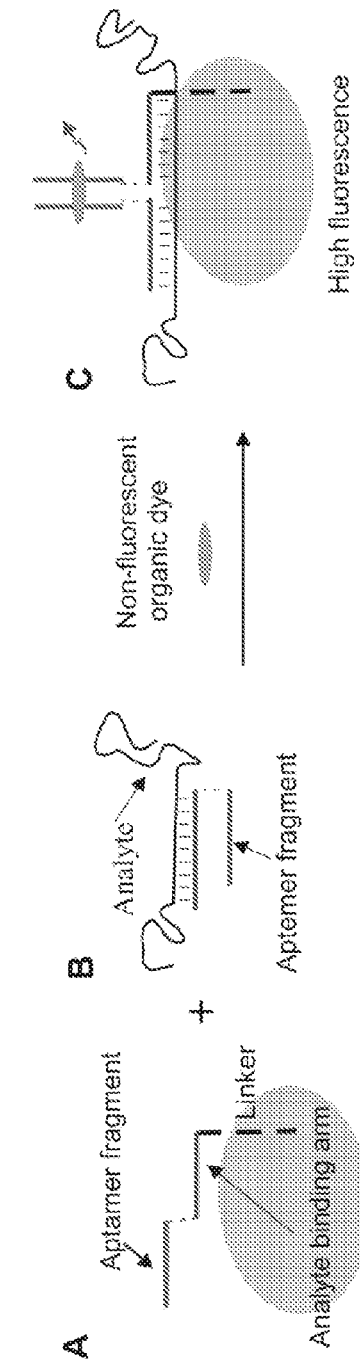
FIG. 10. Is a schematic representation of a nucleic acid aptamer-based microarray of binary probes.

Molecular beacon-binding arms on each strand are typically 3-20 nucleotides long, but routine experimentation based on the molecular beacon will determine the optimum length. FIG. 8. The molecular beacon-binding arms need to be long enough to separate the fluorophore on the MB from the quencher to facilitate fluorescence only when the molecular beacon is bound to the probe. Although most molecular beacons are DNA oligonucleotides, there is no technical obstacle to making molecular beacons that are RNA or chimeras of DNA and RNA for use in the new binary RNA oligonucleotide probes. Specific examples of binary molecular beacon- or dye-binding probes are described in our earlier work, PCT/US2007/065744, incorporated herein by reference, (See Also: Tyagi, S., Kramer, F. R. 1996. Molecular beacons: probes that fluoresce upon hybridization. *Nat. Biotechnol.* 14: 303-308. 10. Bonnet, G., Tyagi, S., Libchaber, A., Kramer, F. R. 1999. Thermodynamic basis of the enhanced specificity of structured DNA probes. Proc. Natl. Acad. Sci. U.S.A. 96: 6171-6176. 11. Marras, S. A., Tyagi, S., Kramer, F. R. 2006. Real-time assays with molecular beacons and other fluorescent nucleic acid hybridization probes *Clin. Chim. Acta.* 363: 48-60.)

Where dye-binding probes are used, there is a measurable change in dye properties (for example fluorescence, phosphorescence or electronic spectra) upon binding to analyte, which is easily and instantly detectable. In one embodiment the binary dye-binding probe is an unmodified RNA oligonucleotide malachite green aptamer (MGA). An aptamer is a type of synthetic oligonucleotide that can bind to a particular target molecule, in this case a molecule is capable of generating a detectable signal. FIG. 10. Is a schematic representation of a nucleic acid aptamer-based microarray of binary probes. The MGA is an RNA molecule that has submicromolar affinity to malachite green (MG), a triphenylmethane dye. Upon binding to analyte, MGA increases the fluorescence of the dye >2000 fold. (Babendure, J. R., J. Am. Chem. Soc. 2003, 125, 9266-9270), incorporated herein by reference. When the target nucleic acid hybridizes to the analyte-binding arms, the probe binds to the MG dye and a detectable fluorescent signal is generated. See FIG. 9. Other aptamers that can be modified for use as a binary dye probe include a modified sulforodamine B aptamer (for the probe), and a sulforodamine dye, including but not limited to patent blue violet or patent blue VF. Other dyes that come within the scope of the invention include triphenylmethane dyes like malachite green, including bis (N-methylindoliny), and Malichite Green IMG.

Certain embodiments of the invention are drawn to new binary reporter oligonucleotide probes that can also be used in the new microarrays. Reporter Oligonucleotide (RO) means an oligonucleotide to which a reporter molecule is linked, such as a gold nanoparticle, fluorescent molecule, quantum dot or any reporter that can be detected. Each antiparallel strand of binary reporter oligonucleotide probes have a reporter oligonucleotide-binding arm that is complementary to and hybridizes to a portion of the RO, and analyte-binding arms. RO probes optionally have substrate stabilization arms, and stem regions. The RO-binding arms and the ABA are either linked by phosphodiester bonds between nucleotides at the joined ends, or by added linkers that can be nucleotide or nonnucleotide, as described herein. The RO probes generate a detectable signal only when the ABA bind to target analyte. RO probes optional have substrate stabilization arms and linkers as described herein. In some embodiments the RO sequence is independent of the analyte sequence: this enables using only one universal reporter molecule for analysis of almost any RNA/DNA analyte, which reduces the cast of such assays.

An example of SNP analysis using a nonenzymatic molecular beacon-binding probe is shown in FIG. 4. In this embodiment the first strand of the probe is immobilized on a support via a flexible linker to the analyte-binding arm (FIG. 4A). The second strand of the probe is separate and hybridized to the analyte in solution to form a hybrid (FIG. 4B). The hybrid is then incubated with the support in the presence of the complementary molecular beacon. Only in the case of fully complementary analyte the fluorescent complex (FIG. 4C) is formed. A single mismatch prevents molecular beacon-binding to the probe, FIG. 4D. Another embodiment of binary dye-binding probe is Hoechst dye-binding aptamer developed by Sando et al. (Sando S, Narita A, Aoyama Y. Light-up Hoechst-DNA aptamer pair: generation of an aptamer-selective fluorophore from a conventional DNA-staining dye Chembiochem. 2007 Oct. 15; 8(15):1795-803.

Microarray Fabrication

Microarrays can be fabricated using a variety of technologies, including printing with fine-pointed pins onto glass slides, photolithography using pre-made masks, photolithography using dynamic micromirror devices, ink-jet printing or electrochemistry on microelectrode arrays. Various methods for making microarrays on which nucleic acid probes are immobilized are well known in the art. Some are discussed in Todd, et al., U.S. Ser. No. 11/544,926.

In spotted microarrays, the probes are oligonucleotides probes are synthesized prior to deposition on the array surface and are then "spotted" onto glass. A common approach utilizes an array of fine pins or needles controlled by a robotic arm that is dipped into wells containing DNA probes and then depositing each probe at designated locations on the array surface. The resulting "grid" of probes represents the nucleic acid profiles of the prepared probes and is ready to receive complementary nucleic acid analyte "targets" derived from experimental or clinical samples. These arrays may be easily customized for each experiment, because researchers can choose the probes and printing locations on the arrays, synthesize the probes in their own lab (or collaborating facility), and spot the arrays.

It is possible to make certain microarrays of binary probes as an "oligonucleotide array," referring to a specific technique of manufacturing. Oligonucleotide arrays are produced by printing short oligonucleotide sequences or synthesizing the sequences directly onto the array surface instead of depositing intact sequences. Sequences may be up to 60-mer probes depending on the desired purpose. Shorter probes such as those in the binary probes may be spotted in higher density across the array and are cheaper to manufacture.

The photolithographic synthesis of microarrays (such as is used by Agilent and Affymetrix) is done on a silica substrate where light and light-sensitive masking agents are used to "build" a sequence one nucleotide at a time across the entire array. Each applicable probe is selectively "unmasked" prior to bathing the array in a solution of a single nucleotide, then a masking reaction takes place and the next set of probes are unmasked in preparation for a different nucleotide exposure. After many repetitions, the sequences of every probe become fully constructed. Any method known in the mart for making the arrays and immobilizing one or both halves of the binary probes on the array can be used in the present invention.

Kits

In an embodiment the microarray is provided as a kit that includes a solid support on which the first strands of a plurality of binary probes are fixed to particular known sites on the microarray, and the respective second strands are provided separately. The kit optionally includes the appropriate reporter. Since the hybridization can take place at physiologic conditions, it is possible to put different types of binary probes on the same microarray, for example, mixing enzymatic and nonenzymatic probes, or different types of each. The present invention also provides kits for using the microarrays of the present invention. For example, in one embodiment a kit may comprise in a first container, a microarray of features of immobilized binary probe complexes, and in a second container the appropriate molecules needed to generate a detectable signal when the probes bind the target analyte. Where the probes are enzymatic probes, the kit may further include the appropriate enzyme substrate or substrates. If peroxidase like probes are on the array, then the kit would include hemin and for example DAB. Where the probes are nonenzymatic, the kit may include the molecular beacons or dyes to which the probes hybridize. If enzymatic and nonenzymatic probes are immobilized on the microarray, suitable substrates for the enzyme(s) and signal-generating molecular beacons or dyes are included in the kit. In those embodiments where only one strand of the plurality of binary probes are immobilized on the array, the kit would further include the second strand of each of the plurality of immobilized probes in a separate container. In some embodiments the probes may not have analyte-binding arms, which are added by the users.

Typically, the kits of the present invention will also include one or more other containers, containing for example, wash reagents, and/or other reagents as required in the performance of the methods of the invention. The kits may be compartmentalized and may also include containers may allow the efficient transfer of reagents from one compartment to another compartment without cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent. Typically, a kit of the present invention will also include instructions for using the kit components to conduct the appropriate methods.

In embodiments where a binary peroxidase-like enzyme probe is immobilized on the microarray, the probes bind hemin from solution, which catalyzes the degradation of hydrogen peroxide to products that in turn oxidize a number of different (secondary) substrates including DAB (3,3'-diaminobenzidine) to water insoluble oxidation products that stain the microarray feature in brown for visual detection. In this format the signal may be detected by naked eye and/or by a conventional scanner. Kits that include microarrays on which one or both strands of a binary peroxidase-like probe are immobilized will also optionally include hemin, hydrogen peroxide and the substrates that can be oxidized by the peroxidase reaction products.

EXAMPLES

In the following Examples the specificity of the binary probes for detecting a specific target nucleic acid analyte were carried out in solution. The two oligonucleotide strands of the probe were not linked to one another and neither strand was bound to a microarray, hereafter "free binary probes." A person of skill in the art can adapt these protocols for use with the microarrays of the present invention.

DNAse/RNAse free water was purchased from Fisher Scientific Inc. (Pittsburgh, Pa.) and used for buffers, and for stock solutions of oligonucleotides. Oligonucleotides were custom-made by Integrated DNA Technologies, Inc. (Coralville, Iowa) or by TriLink BioTechnologies, Inc (San Diego, Calif.). Fluorescent spectra can be taken on a Perkin-Elmer (San Jose, Calif.) LS-55 Luminescence Spectrometer with a Hamamatsu Xenon lamp. Electronic spectra can be taken on a Spectrophotometer Ultraspec 3300 (Amersham-Biotech, NJ, USA). The data can be processed using Microsoft Excel.

Example 1

Peroxidase-like Binary Probes

Details for making free binary oligonucleotide peroxidase probes and for and testing them in solution for SNP analysis, are set forth in U.S. Provisional Application 61/117,081. Oligonucleotides were custom-made by Integrated DNA Technologies, Inc. (Coralville, Iowa). Hydrogen peroxide, 3-3'-diaminobenzidine tetrahydrochloride (DAB), 2,2'-azino-bis (3-ethylbenzthiazoline-6-sulphonic acid) (ABTS), hemin, and HEPES were from Sigma-Aldrich (St. Louis, Mo., USA).

B. SNP typing assay. The free binary peroxidase-like DNA enzymes (1 µM both strands) were incubated in the reaction buffer (50 mM HEPES, pH 7.4, 50 mM $MgCl_2$, 20 mM KCl, 120 mM NaCl, 0.03% Triton X-100, 1% DMSO, hemin (125 nM), $H_2O_2$ (1 mM), and DAB or ABTS (1 mM)) in the absence or presence of analyte. Negative control (sample 0) would have no oligonucleotides. For SNP typing of free probes in solution the electronic absorption spectra of the samples were recorded after 30 min of incubation with the analyte at room temperature, and the test tubes were photographed using Olympus FE-170 digital camera 6 mega pixels.

Native PAGE can be used to test the binary probes. The reaction mixtures containing analyte bound to free peroxidase probe were analyzed in 12% native PAGE containing the reaction buffer. Each reaction mixture can be mixed 1:10 with the loading buffer (50% Glycerol, 50 mM HEPES, pH 7.4, 50 mM $MgCl_2$, 20 mM KCl, 120 mM NaCl, 0.03% Triton X-100, 1% DMSO, 0.01% bromphenol, 0.01% xylencyanol). Two microliters of each sample can be loaded on the gel and run 1 h at room temperature (200 V) followed by staining with SYBR Gold (Invitrogen, OR) and photographed using Alphaimager 3400 (Alpha Innotech, CA).

Substrates for Peroxidase Probes ABTS (2,2'-azino-bis(3-ethylbenzthiazoline-6-sulphonic acid) is a commonly used water soluble substrate of hydrogen peroxidases. Therefore, DAB can be substituted with ABTS in the colorimetric assay for SNP. Addition of analyte should make the color of solution containing binary DNA peroxidase probe turn green; this color would be visually distinct from the solution containing mismatched rs242557-A or no analyte. ABTS can replace DAB in the SNP typing assay, but with substantial reduction of S/B (from ~10 to ~6).

Dithymidine Linkers Triethylene glycol linkers in the sequence of the binary DNA peroxidase probe are preferred. Dithymidine linkers can be used, however, it is possible that in certain embodiments the intensity of the optical signal may be reduced. We found that the signal was reduced about 6 times when dithymidine linkers were used with the peroxidase-like probe described in a. above, generating a weak color that was hardly recognizable by the naked eye (data not shown). At the same time, the probes composed of $\alpha\beta_{tt}$ and $\alpha_{tt}\beta$ generated color intensive enough to be visualized in a test tube. The highest signal-to-background ratios were found for $\alpha_{tt}\beta_{tt}$ and $\alpha\beta_{tt}$ combinations, ~46 and ~30, respectively, due to a very low background reaction. In all cases the probes were highly selective and generated no signal above the background in the presence of the mismatched analyte in solution. These data show that at least one strand of the probe can be composed of purely natural nucleotides. The cost for chemical incorporation of dithymidine linker is almost 50 times lower than that of the triethylene glycol linker. Therefore, using a nucleotide linker may further reduce the assay cost.

Example 2

Nonenzymatic Binary Nucleic Acid Probes

Source of Molecular Beacons (MB) MBs are robust reagents for detecting and quantitating nucleic acids, even in real time (e.g., MBs can be used to detect targets as they are formed). A variety of commercial suppliers produce standard and custom molecular beacons, including Chruachem (chruachem.com), Oswel Research Products Ltd. (UK; oswel.com), Research Genetics (a division of Invitrogen, Huntsville, Ala. (resgen.com)), the Midland Certified Reagent Company (Midland, Tex. mcrc.com) and Gorilla Genomics, LLC (Alameda, Calif.). A variety of kits which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com, the entire contents of which are hereby incorporated by reference as if fully set forth herein.

Binary Malachite Green-binding Probe

A. Binary Malachite Green Aptamer probe. To test the specificity of the probe, MG (2 µM) and two RNA strands of biMGA probe (1 µM each) were mixed in 5.3 ml of the buffer containing 50 mM TrisHCl pH 7.4, 140 mM NaCl, 5 mM KCl, 1 mM $MgCl_2$. The free probes were incubated with analyte for 15 min at room temperature. Fluorescent spectra were taken on a Perkin-Elmer (San Jose, Calif.) LS-55 Luminescence Spectrometer with a Hamamatsu Xenon lamp.

Experiments can be performed at the excitation wavelength of 610 nm and emission scan of 620-720 nm. The emitting intensities at 648 nM can be used for the calculation of the discrimination factors. The data of four independent experiments were processed using Microsoft Excel.

Example 4

Flexible Linkers The "Int" linkers below, referred to by the manufacturer Integrated DNA technology as "spacers" can be used to make the probes of the present invention.

Int C3 Spacer:
Structure

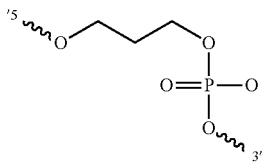

Int Spacer 18

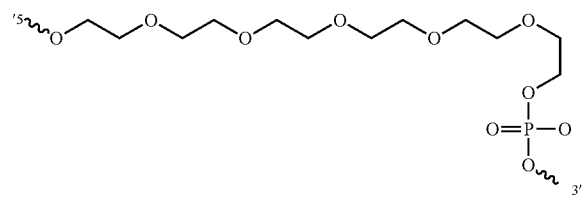

Int dSpacer
Structure

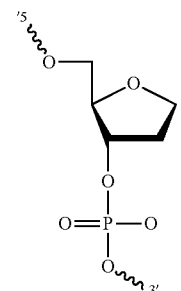

In the foregoing specification, the invention has been described with reference to specific embodiments. It will, however, be evident that various modifications and changes may be made without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

What is claimed:

1. A microarray for detecting a plurality of nucleic acid analytes in a complex sample, comprising a plurality of non-naturally occurring binary nucleic acid probe complexes immobilized at separate sites on a solid support, wherein each complex comprises a binary nucleic acid probe comprising two oligonucleotide strands that generate a detectable signal when each strand is bound to one of the plurality of analytes;

wherein the binary nucleic acid probe is a non-naturally occurring nonenzymatic reporter oligonucleotide-binding binary nucleic acid probe for detecting an oligonucleotide analyte comprising two oligonucleotide strands wherein 1. a first oligonucleotide strand comprises: a. at its 5'-terminus a reporter oligonucleotide-binding arm that is complementary to and selectively hybridizes with a reporter oligonucleotide to which a reporter that can be detected is bound, and b. at its 3'-terminus an analyte-binding arm that is complementary to and selectively hybridizes with a first region of the oligonucleotide analyte, and 2. a second oligonucleotide strand comprises: a. at its 3'-terminus a reporter oligonucleotide-binding arm that is complementary to and selectively hybridizes with a reporter oligonucleotide to which a reporter that can be detected is bound, and b. at its 5'-terminus, an analyte-binding arm that is complementary to and selectively hybridizes with a second region of the oligonucleotide analyte; and wherein the analyte binding arm of one strand of each of the plurality of binary probe complexes is covalently bound to the solid support by a linker.

2. The microarray of claim 1, wherein the two oligonucleotide strands of the binary probe are bound to one another by a linker.

3. The microarray of claim 1, wherein the binary probe binds to a molecular beacon, dye or a labeled reporter oligonucleotide generating a fluorescent signal when both analyte-binding arms are bound to the analyte.

4. The microarray as in claim 1, wherein the linker is a member selected from the group comprising epoxy-silane, amino-silane, lysine, and polyacrylamide.

5. The microarray of claim 2, wherein first and second oligonucleotide strands are linked to one another though a linker that is a member of the group comprising T, C, dinucleotides including CC and TT, trinucleotides including TTT and CCC, oligoethylene glycol, hexa-ethyleneglycol and triethylene glycol.

6. The microarray of claim 1, wherein the solid support is a member selected from the group comprising an organic polymer, glass, silicon, optical fiber, carbon nanotube, gold nanoparticle, or gold covered surface of a sensor.

7. The microarray of claim 1, wherein the binary probe binds to a labeled reporter oligonucleotide generating a signal that can be detected by optical, electrical or magneto electrical means when both analyte-binding arms are bound to the analyte.

* * * * *

UNITED STATES PATENT AND TRADEMARK OFFICE
CERTIFICATE OF CORRECTION

PATENT NO. : 8,853,134 B2
APPLICATION NO. : 13/146626
DATED : October 7, 2014
INVENTOR(S) : Dmitry Kolpashchikov It is certified that error appears in the above-identified patent and that said Letters Patent is hereby corrected as shown below:

In the Specification

On Column 1, Line 5, please replace the paragraph titled STATEMENT OF GOVERNMENTAL INTEREST with the following:
--This invention was made with government support under grants EB000675 and HG004060 awarded by the National Institutes of Health and grant BES0321972 awarded by the National Science Foundation. The government has certain rights in the invention.--

Signed and Sealed this
Seventh Day of November, 2023

Katherine Kelly Vidal
*Director of the United States Patent and Trademark Office*